United States Patent [19]
Seto et al.

[11] Patent Number: 5,626,740
[45] Date of Patent: May 6, 1997

[54] METHOD OF AND APPARATUS FOR MEASURING ELECTROLYTE

[75] Inventors: Shunichi Seto, Kanagawa-ken; Kenichiro Yazawa; Osamu Seshimoto, both of Saitama-ken, all of Japan

[73] Assignee: Fuji Photo Film Co., Ltd., Kanagawa-ken, Japan

[21] Appl. No.: 587,249

[22] Filed: Jan. 16, 1996

Related U.S. Application Data

[63] Continuation of Ser. No. 305,027, Sep. 13, 1994, abandoned.

[30] Foreign Application Priority Data

Sep. 14, 1993 [JP] Japan .................................. 5-228415

[51] Int. Cl.$^6$ ...................................... G01N 27/26
[52] U.S. Cl. ............... 205/789; 205/775; 205/781.5; 205/782.5; 205/793; 204/416; 204/418; 204/435; 73/864.24; 73/864.25; 422/82.03; 141/248; 141/130
[58] Field of Search ...................... 204/416, 418, 204/435, 400, 412, 153.1, 153.17, 153.15; 73/864.24, 864.25; 422/82.03; 141/248, 130; 205/782.5, 781.5, 775, 789, 793

[56] References Cited

U.S. PATENT DOCUMENTS

| | | | |
|---|---|---|---|
| 3,767,364 | 10/1973 | Ritchie et al. | 141/130 |
| 4,053,381 | 10/1977 | Hamblen et al. | 204/195 M |
| 4,341,736 | 7/1982 | Drbal et al. | 73/864.25 |
| 4,347,750 | 9/1982 | Tersteeg et al. | 73/864.31 |
| 4,437,970 | 3/1984 | Kitajima et al. | 204/412 |
| 4,789,435 | 12/1988 | Seshimoto et al. | 204/416 |
| 4,801,434 | 1/1989 | Kido et al. | 422/100 |
| 5,213,764 | 5/1993 | Kerr et al. | 73/864.25 |
| 5,330,625 | 7/1994 | Muszak et al. | 204/416 |

*Primary Examiner*—Bruce F. Bell
*Attorney, Agent, or Firm*—McAulay Fisher Nissen Goldberg & Kiel, LLP

[57] ABSTRACT

When determining an activity of particular predetermined ions in a sample liquid by use of a device for measuring ionic activity including a pair of ion-selective electrodes which are selectively responsive to particular predetermined ions, a pair of spotting holes through which a sample liquid and a reference liquid are respectively supplied to the ion-selective electrodes and a porous bridge which communicates the spotting holes with each other so as to permit the sample liquid and the reference liquid spotted to the spotting holes to electrically contact with each other, for instance, the sample liquid is first spotted to one of the spotting holes of the device for measuring ionic activity with a first spotting tool, and at least one of the first spotting tool and the device for measuring ionic activity is thereafter moved to remove the first spotting tool away from the device for measuring ionic activity. Then the reference liquid is spotted to the other spotting hole of the device for measuring ionic activity with a second spotting tool within a predetermined time after the sample liquid is spotted to the spotting hole.

9 Claims, 2 Drawing Sheets ic activity.

METHOD OF AND APPARATUS FOR MEASURING ELECTROLYTE

This is a continuation of application Ser. No. 08/305,027 filed Sep. 13, 1994 now abandoned.

BACKGROUND OF THE INVENTION

1. Field of the Invention

This invention relates to a method for measuring electrolyte and an apparatus for measuring electrolyte for measuring the concentration (activity) of particular predetermined ions in an aqueous solution such as liquor, city water and body fluids (e.g., blood, blood plasma, blood serum, lymph, cerebrospinal fluid and urine) in potentiometric way by use of a device for measuring ionic activity.

2. Description of the Prior Art

There is disclosed, for instance in U.S. Pat. Nos. 4,053,381 and 4,437,970, a device for measuring ionic activity which makes it feasible to determine the activity of particular predetermined ions in sample liquid from a droplet of the sample liquid deposited thereon by spotting.

The device for measuring ionic activity comprises a pair of ion-selective electrodes each of which generates a potential corresponding to the activity of particular predetermined ions, a pair of spotting holes through which a sample liquid (a liquid wherein the activity of particular predetermined ions is unknown) and a reference liquid (a liquid wherein the activity of the particular predetermined ions is known) are respectively supplied to the ion-selective electrodes and a porous bridge for ionic contact which communicates the spotting holes with each other. In the device for measuring ionic activity, the activity of the particular predetermined ions in the sample liquid is determined in the following manner. That is, when the sample liquid is supplied through one of the spotting holes and the reference liquid is supplied through the other spotting hole, the liquids are applied to the respective ion-selective electrodes and at the same time diffuse in the porous bridge by capillarity to come into contact with each other at a liquid phase boundary. This contact between the sample liquid and the reference liquid establishes an electrical conduction between the electrodes, and a potential difference is generated between the electrodes according to the difference in the activity of the particular predetermined ions between the sample liquid and the reference liquid. By measuring the potential difference, the activity of the particular predetermined ions in the sample liquid can be determined.

It has been believed that, in order to determine the activity of the particular predetermined ions in the sample liquid with high accuracy, the sample liquid and the reference liquid must form a phase boundary at the center of the porous bridge. Accordingly, the sample liquid and the reference liquid are conventionally spotted to the spotting holes simultaneously with each other. As a device for facilitating such simultaneous spotting, there has been known a dual pipette device disclosed, for instance, in U.S. Pat. No. 4,801,434.

Though the dual pipette device is for manually spotting the sample liquid and the reference liquid, it is preferred that spotting of the liquids be automated in order to measure a number of sample liquids at high speed. In U.S. Pat. No. 4,347,750, there is disclosed a device for automating spotting of the sample liquid and the reference liquid. In the device, a reference liquid spotting tip which sucks a reference liquid in a reference liquid sucking position and spots the reference liquid to one of the spotting holes in the device for measuring ionic activity in a reference liquid spotting position is arranged to be movable between the reference liquid sucking position and the reference liquid spotting position independently from a sample liquid spotting tip which sucks a sample liquid in a sample liquid sucking position and spots the sample liquid to the other spotting hole in a sample liquid spotting position. In the reference liquid spotting position, the reference liquid spotting tip is held obliquely though the sample liquid spotting tip is held vertically in the sample liquid spotting position. This is for the following reason. That is, in order to simultaneously spot the sample liquid and the reference liquid, the spotting tips must be simultaneously positioned above the corresponding spotting holes. However since the space between the spotting holes is generally narrow (e.g., 8 mm), the parts for holding the spotting tips interfere with each other when the spotting tips are positioned above the spotting holes with both the spotting tips held vertically. By obliquely holding the reference liquid spotting tip, interference between the parts for holding the spotting tips is prevented and the sample liquid and the reference liquid can be simultaneously spotted.

However when the reference liquid spotting tip is held obliquely, it is difficult to accurately spot the reference liquid to the spotting hole. Further the mechanism for obliquely holding the reference liquid spotting tip is complicated in structure, which increases the cost of the overall apparatus. As a result, the cost of measurement of electrolytes by use of the device for measuring ionic activity increases.

SUMMARY OF THE INVENTION

In view of the foregoing observations and description, the primary object of the present invention is to provide a method for measuring electrolyte and an apparatus for measuring electrolyte which makes it feasible to accurately spot the sample liquid and the reference liquid to the spotting holes of the device for measuring ionic activity, to determine the activity of particular predetermined ions in the sample liquid with a high accuracy and to measure a number of sample liquids at a high rate at low cost.

In the method for measuring electrolyte of the present invention, the activity of particular predetermined ions in a sample liquid is measured by use of a device for measuring ionic activity comprising an ion-selective pair consisting of a pair of ion-selective electrodes which are selectively or specifically responsive to the same particular predetermined ions, a pair of spotting holes through which a sample liquid and a reference liquid are respectively supplied to the ion-selective electrodes and a porous bridge which communicates the spotting holes with each other so as to permit the sample liquid and the reference liquid spotted to the spotting holes to electrically contact with each other. The method of the present invention comprises the steps of spotting one of the sample liquid and the reference liquid to one of the spotting holes of the device for measuring ionic activity with a first spotting tool, thereafter moving at least one of the first spotting tool and the device for measuring ionic activity to remove the first spotting tool away from the device for measuring ionic activity, and then spotting the other of the sample liquid and the reference liquid to the other spotting hole of the device for measuring ionic activity with a second spotting tool within a predetermined time after said one of the sample liquid and the reference liquid is spotted to said one of the spotting holes.

The expression "moving at least one of the first spotting tool and the device for measuring ionic activity to remove the first spotting tool away from the device for measuring ionic activity" means that the first spotting tool may be removed away from the device for measuring ionic activity (to prevent interference between the first and second spotting tools) by moving both the first spotting tool and the device for measuring ionic activity, or by moving only the device for measuring ionic activity with the first spotting tool held stationary, or by moving only the first spotting tool with device for measuring ionic activity held stationary.

The apparatus for measuring electrolyte of the present invention comprises a support table which supports a device for measuring ionic activity comprising an ion-selective electrode pair consisting of a pair of ion-selective electrodes which are selectively responsive to the same particular predetermined ions, a pair of spotting holes through which a sample liquid and a reference liquid are respectively supplied to the ion-selective electrodes and a porous bridge which communicates the spotting holes with each other so as to permit the sample liquid and the reference liquid spotted to the spotting holes to electrically contact with each other, and positions the device for measuring ionic activity in a predetermined position where the sample liquid and the reference liquid are to be spotted to the respective spotting holes, a sample liquid spotting means including a sample liquid spotting tool which holds the sample liquid and spots the same to one of the spotting holes of the device for measuring ionic activity and a transfer mechanism which moves the sample liquid spotting tool between a spotting position where it spots the sample liquid to said one of the spotting holes of the device for measuring ionic activity positioned in said predetermined position and a retracted position away from the spotting position, and a reference liquid spotting means including a reference liquid spotting tool which holds the reference liquid and spots the same to the other spotting hole and a transfer mechanism which moves the reference liquid spotting tool between a spotting position where it spots the reference liquid to said the other spotting hole of the device for measuring ionic activity positioned in said predetermined position and a retracted position away from the spotting position, the two spotting means being arranged so that one of the first and second spotting means first spots the corresponding liquid to the corresponding spotting hole in its spotting position and is removed away from the spotting position and then the other spotting means is moved to its spotting position to spot the corresponding liquid to the corresponding spotting hole within a predetermined time after said one spotting means spots the corresponding liquid to the corresponding spotting hole.

The lower limit of said predetermined time is naturally depending on a minimum time interval required to remove said one spotting means away from its spotting position and to subsequently move said the other spotting means to its spotting position. The upper limit of said predetermined time differs depending on the type of device for measuring ionic activity used. In one type of device for measuring ionic activity, the porous bridge is formed of twisted yarn of polyester or the like and is positioned apart from the ion-selective electrodes. In the device for measuring ionic activity of this type, the ion-selective electrodes are not electrically connected with each other until both the spotting holes are spotted with liquid. In another type of device for measuring ionic activity, the porous bridge is formed of a thin film of filter paper or the like and is in a direct contact with the ion-selective electrodes. In the device for measuring ionic activity of this type, the ion-selective electrodes come to be electrically connected with each other in a certain time after one of the spotting holes is spotted with liquid even if the other spotting hole is not spotted with liquid. In the former type device for measuring ionic activity, the upper limit depends on the time over which the liquid spotted first will dry or vapor to adversely affect the measurement. In the latter type device for measuring ionic activity, the upper limit depends on the time over which the liquid spotted first to one spotting hole will reach the other spotting hole through the porous bridge to electrically connect the ion-selective electrodes with each other.

In accordance with the present invention, the sample liquid spotting tool and the reference liquid spotting tool are not simultaneously positioned above the spotting holes. Accordingly, either of them need not be held obliquely upon spotting unlike the conventional system but both of them may be held vertically, whereby both the sample liquid and the reference liquid can be accurately spotted to the spotting holes of the device for measuring ionic activity and the activity of particular predetermined ions in the sample liquid can be determined with a high accuracy. Further since either of the spotting tools need not be held obliquely upon spotting, the mechanisms for driving the spotting tools may be simple in structure and the spotting operation can be automated at low cost. As a result, a number of sample liquids can be measured at a high rate at low cost.

DESCRIPTION OF THE PREFERRED EMBODIMENT

Figure 1:
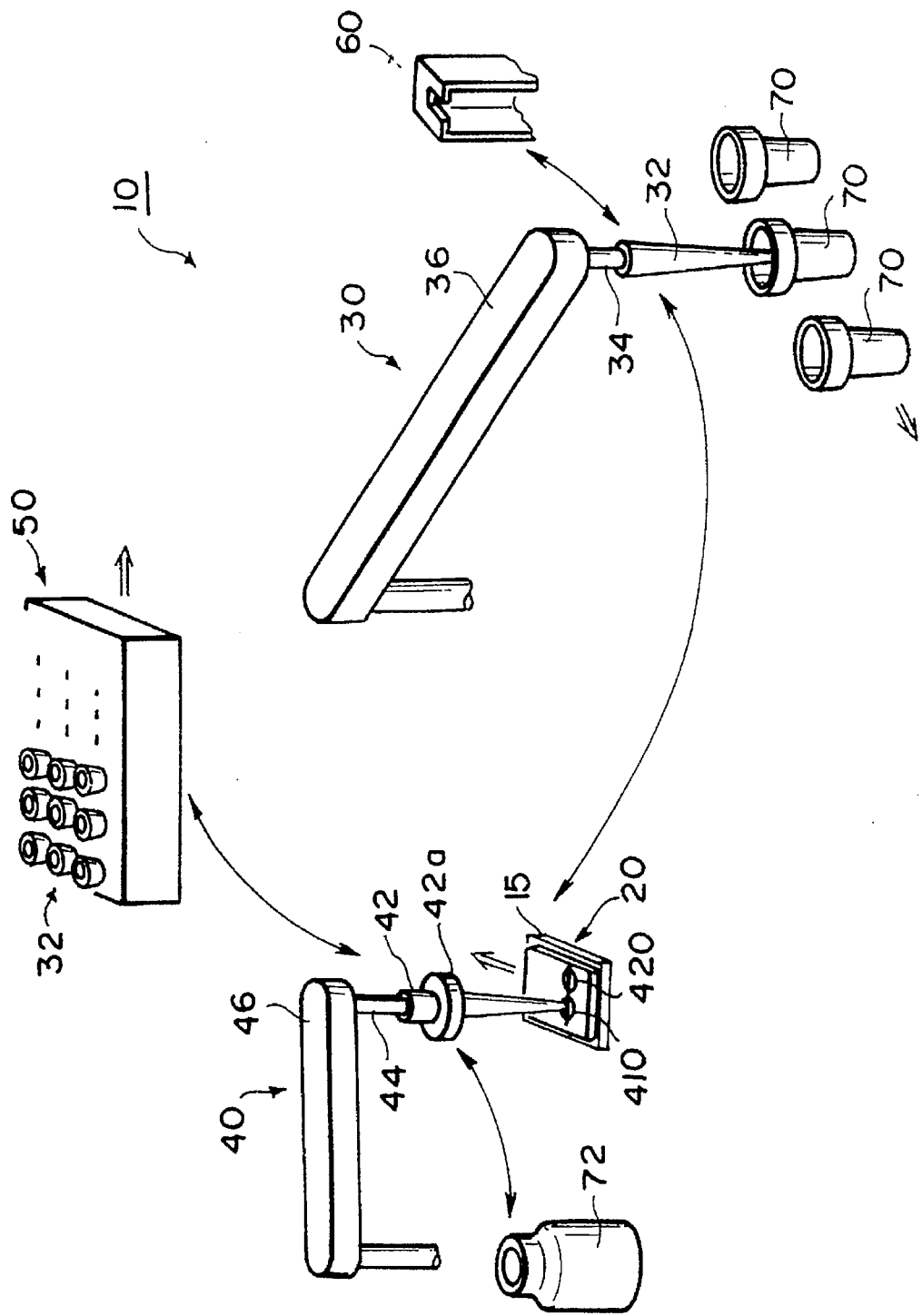
FIG. 1 is a schematic perspective view showing an apparatus for measuring electrolyte in accordance with an embodiment of the present invention.

In FIG. 1, an apparatus for measuring electrolyte 10 of this embodiment comprises a support table 15 which supports a device for measuring ionic activity 20 and positions it in a predetermined position in a spotting station (not shown) for spotting a sample liquid and a reference liquid, a sample liquid spotting means 30 which spots the sample liquid to one of first and second spotting holes 410 and 420 of the device for measuring ionic activity 20 (in this particular embodiment to the second spotting hole 420) and a reference liquid spotting means 40 which spots the reference liquid to the other spotting hole or the first spotting hole 410. The activity of particular predetermined ions is unknown in the sample liquid and is known in the reference liquid.

Figure 2:
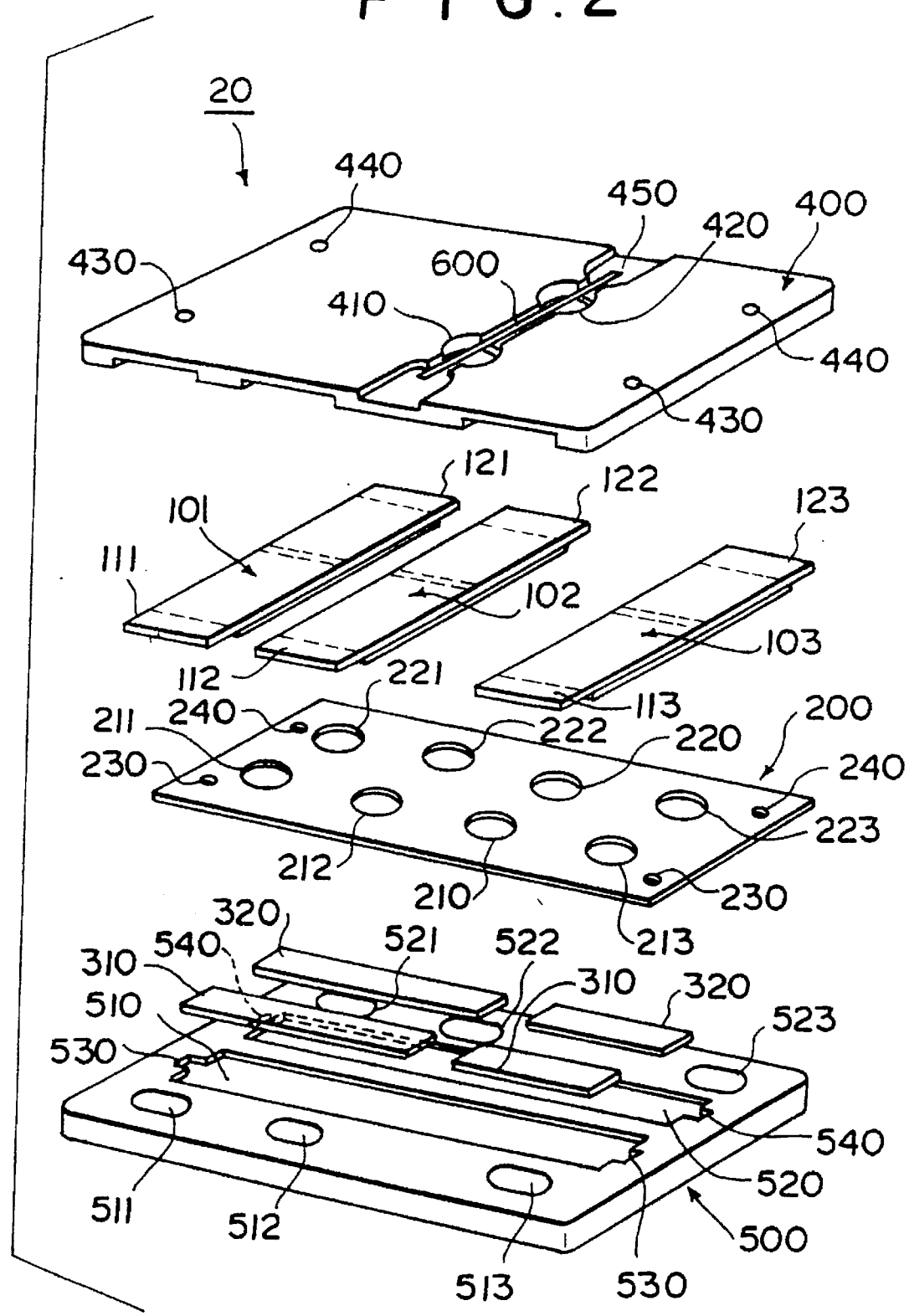
FIG. 2 is an exploded perspective view of an example of a device for measuring ionic activity employed in the apparatus shown in FIG. 1.

The device for measuring ionic activity 20 may be of a known type such as disclosed, for instance, in U.S. Pat. Nos. 4,053,381, or 4,437,970. An example of the structure of device for measuring ionic activity 20 will be briefly described with reference to FIG. 2, hereinbelow. As shown in FIG. 2, the device for measuring ionic activity 20 comprises three ion-selective electrode pairs 101, 102 and 103, a water-impermeable layer member 200 which is impermeable to water and is provided with an adhesive layer on each side thereof and a pair of porous liquid distributor members 310 and 320 which are sandwiched between upper and lower frame members 400 and 500. Each of the ion-selective electrode pairs comprises a pair of ion-selective electrodes (111 and 121; 112 and 122; 113 and 123) which are provided with the same ion-selective layers on the surfaces and electrically isolated from each other. The ion-selective layers of the ion-selective electrode pairs differ from pair to pair. The porous liquid distributor members 310 and 320 are made of, for instance, nonwoven fabrics of cotton and regenerated cellulosic fibers having interconnected pores. Each of the porous liquid distributor members 310 and 320 is cut into two pieces in alignment with each other in the longitudinal direction of the device for measuring ionic activity 20.

The upper frame member 400 is provided with the first and second spotting holes 410 and 420 arranged in the transverse direction thereof, and an elongated recess 450 extending in the transverse direction of upper frame member 400 across the spotting holes 410 and 420. A porous porous bridge 600 which is made of, for instance, spun yarn of polyethylene terephthalate fibers is fixed in the recess 450. The recess 450 has such a depth that the porous bridge 600 does not project from the upper surface of the upper frame member 400.

The water-impermeable layer member 200 which is disposed under the upper frame member 400 with the ion-selective electrode pairs 101, 102 and 103 intervening therebetween is provided with through holes (downward passage) 210 and 220 which are respectively aligned with the spotting holes 410 and 420 and through holes (upward passage) 211, 212, 213, 221, 222 and 223 which are respectively opposed to parts of the ion-selective layer of the ion-selective electrodes 111, 112, 113, 121, 122 and 123. The liquid distributor members 310 and 320 are disposed under the water-impermeable layer member 200 so that the former member 310 is opposed to the through holes 210, 211, 212 and 213 and the latter member 320 is opposed to the through holes 220, 221, 222 and 223. The liquid distributor members 310 and 320 are respectively received in recesses (horizontal passages) 510 and 520 formed in the lower frame member 500. Two pairs of through holes (430 and 440; 230 and 240; 530 and 540) are formed in each of the upper frame member 400, the water-impermeable layer member 200 and the lower frame member 500. The through holes form vent holes of the device for measuring ionic activity 20 in the assembled state. The ion-selective electrode pairs 101, 102 and 103 are positioned with the ion-selective layers faced toward the lower frame member 500 and the terminal portions of the electrode pairs are exposed from the lower surface of the device for measuring ionic activity 20 through three pairs of through holes 511 and 521; 512 and 522 and 513 and 523 formed in the lower frame member 500.

Assuming that the ion-selective electrode pairs 101, 102 and 103 respectively have ion-selective layers for $Cl^-$ ions, $K^+$ ions and $Na^+$ ions, when a reference liquid wherein the activities of these ions are known is spotted to the first spotting hole 410 and the sample liquid wherein the activities of these ions are unknown is spotted to the second spotting hole 420, the reference liquid travels to the porous liquid distributor member 310 through the downward passage formed by the through hole 210, soaks into the porous liquid distributor member 310 and then reaches the ion-selective layers of the ion-selective electrodes 111, 112 and 113 through upward passages formed by the through holes 211, 212 and 213 while the sample liquid travels to the porous liquid distributor member 320 through the downward passage formed by the through hole 220, soaks into the porous liquid distributor member 320 and then reaches the ion-selective layers of the ion-selective electrodes 121, 122 and 123 through upward passages formed by the through holes 221, 222 and 223. Further the reference liquid and the sample liquid come into an electrical contact with each other in the porous bridge 600. As a result, potential differences are generated between the electrodes 111 and 121 of the ion-selective electrode pair 101, between the electrodes 112 and 122 of the ion-selective electrode pair 102 and between the electrodes 113 and 123 of the ion-selective electrode pair 103 according respectively to the differences in the activities of $Cl^-$ ions, $K^+$ ions and $Na^+$ ions between the reference liquid and the sample liquid. The potential differences can be measured by bringing potential measuring probes into contact with the terminal portions of the ion-selective electrodes through the through holes 511 and 521; 512 and 522 and 513 and 523 in the lower frame member 500 and the activities of the aforesaid ions in the sample liquid can be determined through the potential differences.

Again in FIG. 1, the support table 15 positions the device for measuring ionic activity 20 placed thereon to the predetermined position in the spotting station and transfers the device for measuring ionic activity 20 spotted with the sample liquid and the reference liquid to an ionic activity measuring station (not shown).

The sample liquid spotting means 30 comprises an arm 36 which is supported for rotation at one end thereof and is provided with a tip mounting portion 34 at the other end. The tip mounting portion 34 extends downward and a spotting tip 32 (spotting tool) for spotting the sample liquid is demountably mounted on the tip mounting portion 34. The arm 36 is moved up and down and is rotated by a drive mechanism (not shown). That is, the arm 36 is rotated to move the tip 32 on the mounting portion 34 along a circular path and is moved up and down in a predetermined position to move the tip 32 up and down while holding the spotting tip 32 in a vertical position. The arm 36 and the drive mechanism form a transfer mechanism of the sample liquid spotting means. The sample liquid spotting means 30 is further provided with a suction mechanism (not shown) for sucking a predetermined amount of sample liquid into the spotting tip 32 and discharging the sample liquid from the tip 32 in a predetermined spotting position in the spotting station to spot the sample liquid to the second spotting hole 420 of the device for measuring ionic activity 20.

The spotting tip 32 is changed every time the sample liquid is changed or every time the kind of sample liquid changes. The spotting tips 32 are stored in a tip container 50 before use and is discarded at a tip discarding section 60 after use. The sample liquids are put in sample liquid containers 70 and the sample liquid 70 are successively conveyed to a predetermined sample liquid sucking position by a conveyor means (not shown).

The sample liquid spotting means 30 is arranged to repeat the step of mounting the tip 32 stored in the tip container 50, the step of sucking the sample liquid into the spotting tip 32 from the sample liquid container 70 conveyed to the sample liquid sucking position and holding the sample liquid in the tip 32, the step of moving the tip 32 above the second spotting hole 420 of the device for measuring ionic activity 20 positioned in the predetermined position in the spotting station and spotting the sample liquid to the second spotting hole 420 and the step of discarding the tip 32 at the tip discarding section 60 after spotting. The sample liquid spotting means 30 executes these steps under the control of a control means (not shown) which may comprise, for instance, a microcomputer and software loaded therein.

The reference liquid spotting means 40 comprises an arm 46 which is supported for rotation at one end thereof and is provided with a tip mounting portion 44 at the other end. The tip mounting portion 44 extends downward and a spotting tip 42 (spotting tool) for spotting the reference liquid is demountably mounted on the tip mounting portion 44. The arm 46 is moved up and down and is rotated by a drive mechanism (not shown). That is, the arm 46 is rotated to move the tip 42 on the mounting portion 44 along a circular path and is moved up and down in a predetermined position to move the tip 42 up and down while holding the spotting tip 42 in a vertical position. The arm 46 and the drive mechanism form a transfer mechanism of the reference liquid spotting means. The reference liquid spotting means 40 is further provided with a suction mechanism (not shown) for sucking a predetermined amount of reference liquid into the spotting tip 42 and discharging the reference liquid from the tip 42 in a predetermined spotting position in the spotting station to spot the reference liquid to the first spotting hole 410 of the device for measuring ionic activity 20.

Unlike the sample liquid spotting tip 32, the reference liquid spotting tip 42 is repeatedly used and is provided with a cap portion 42a for preventing evaporation of the reference liquid. The reference liquid is accommodated in a container 72 and is replenished as needed. Normally the reference liquid spotting means 40 waits with the tip 42 inserted into the reference liquid container 72 so that the cap portion 42a closes the mouth of the container 72 and is moved away from the container 72 only when it spots the reference liquid to the device for measuring ionic activity 20. With this arrangement, change in concentration of the reference liquid due to evaporation of water in the reference liquid is minimized.

The reference liquid spotting means 40 repeats the step of waiting while closing the mouth of the container 72, the step of sucking the reference liquid into the spotting tip 42 from the reference liquid container 72 and holding the reference liquid in the tip 42, and the step of moving the tip 42 above the first spotting hole 410 of the device for measuring ionic activity 20 and spotting the reference liquid to the first spotting hole 410. The reference liquid spotting means 40 executes these steps under the control of the control means.

An example of a procedure for measuring electrolyte by the apparatus for measuring electrolyte 10 of this embodiment will be described, hereinbelow.

First the arm 36 of the sample liquid spotting means 30 is rotated to bring the mounting portion 34 to the tip container 50 and a desired tip 32 is mounted on the mounting portion 34. Then the arm 36 is rotated again to move the tip 32 to the sucking position where a sample liquid container 70 containing therein a predetermined sample liquid is conveyed. Then a predetermined amount of the sample liquid is sucked from the container 70 and held therein. Then the arm 36 of the sample liquid spotting means 30 is rotated to move the tip 32 above the second spotting hole 420 of the device for measuring ionic activity 20 on the support table 15 which has been positioned in the predetermined position in the spotting station and the sample liquid is discharged from the tip 32 and is spotted to the second spotting hole 420 in a predetermined amount. Then the arm 36 is rotated to move the tip 32 to the discarding section and the tip 32 is discarded there.

While the sample liquid is spotted to the second spotting hole 420, the reference liquid spotting means 42 is waiting closing the mouth of the container 72 with the cap portion 42a as described above. When the tip 32 of the sample liquid spotting means 30 is removed away from above the device for measuring ionic activity 20 after spotting the sample liquid, a predetermined amount of the reference liquid is sucked into the reference liquid tip 42 (may be sucked in advance), and the tip 42 is drawn out from the container 72. Then the arm 46 of the reference liquid spotting means 40 is rotated to move the tip 42 above the first spotting hole 410 of the device for measuring ionic activity 20 and the reference liquid is spotted to the first spotting hole 410 in a predetermined amount. The support table 15 is held stationary and the device for measuring ionic activity 20 is held in the predetermined position in the spotting station until the reference liquid spotting means 40 spots the reference liquid. After the reference liquid is spotted, the arm 46 is rotated to return the tip 42 to the container 72 and then is moved downward to insert the tip 42 into the mouth of the container 72 to close the mouth with the cap portion 42a. Thereafter the device for measuring ionic activity 20 on the support table 15 is conveyed to the ionic activity measuring station and the activities of the particular predetermined ions in the sample liquid is determined.

By repeating the procedure described above, a number of sample liquids conveyed to the sucking position one by one can be measured at a high rate. Though in the procedure described above the sample liquid is first spotted, the reference liquid may be first spotted.

In order to prove how accurately the activity of particular predetermined ions in the sample liquid can be determined in accordance with the method of the present invention where the sample liquid and the reference liquid are spotted one after the other, there were made some experiments where the result of the measurement in accordance with the method of the present invention was compared with that in accordance with the conventional method where the sample liquid and the reference liquid were spotted simultaneously with each other.

In the experiments, a device for measuring ionic activity of the same type as that shown in FIG. 2 having three ion-selective electrode pairs was used. The ion-selective electrode pairs respectively had ion-selective layers for $Na^+$, $K^+$ and $Cl^-$ ions and the activities of $Na^+$, $K^+$ and $Cl^-$ ions in a sample liquid were determined.

In a first experiment, 50 µL of the reference liquid was first spotted to one of the spotting holes of each device for measuring ionic activity and the same amount of the sample liquid was spotted to the other spotting hole a predetermined time after spotting of the reference liquid. The concentration of each of $Na^+$, $K^+$ and $Cl^-$ ions was determined 60 seconds after spotting of the sample liquid. In a first group of devices for measuring ionic activity, the predetermined time was set to 0 second, that is, the reference liquid and the sample liquid were spotted simultaneously. In second to fifth groups of devices for measuring ionic activity, the predetermined time was set to 5 seconds, 15 seconds, 30 seconds and 60 seconds, respectively. The result is shown in tables 1 to 3. Two sample liquids which were simulation solutions prepared for the experiment were used. One of the sample liquids was of a low concentration and the other sample liquid was of a high concentration. In tables 1 to 3, L denotes the former sample liquid and H denotes the latter sample liquid. Further the concentrations of the ions shown in tables 1 to 3 are the average values of five measurements for each group of the devices for measuring ionic activity and are in mEq/L.

TABLE 1

| (Na+ ion concentration) | | | | | |
|---|---|---|---|---|---|
| | 0 sec. | 5 sec. | 15 sec. | 30 sec. | 60 sec |
| L | 98.2 | 99.0 | 98.8 | 98.8 | 98.6 |
| H | 177.6 | 178.2 | 178.2 | 178.2 | 178.2 |

TABLE 2

| (K+ ion concentration) | | | | | |
|---|---|---|---|---|---|
| | 0 sec. | 5 sec. | 15 sec. | 30 sec. | 60 sec |
| L | 2.6 | 2.6 | 2.6 | 2.6 | 2.6 |
| H | 6.4 | 6.4 | 6.4 | 6.4 | 6.3 |

TABLE 3

| (Cl− ion concentration) | | | | | |
|---|---|---|---|---|---|
| | 0 sec. | 5 sec. | 15 sec. | 30 sec. | 60 sec |
| L | 65.0 | 65.8 | 66.0 | 66.2 | 68.6 |
| H | 133.6 | 134.0 | 134.4 | 135.4 | 138.0 |

As can be seen from tables 1 to 3, the deviation of the results obtained when the sample liquid were spotted 5 seconds, 15 seconds, 30 seconds and 60 seconds after spotting of the reference liquid from that obtained when the sample liquid was spotted simultaneously with the reference liquid are negligible though the deviation for 60 seconds is somewhat large.

In a second experiment, the sample liquid was first spotted and the reference liquid was spotted next. The other conditions were the same as those in the first experiment. The result is shown in tables 4 to 6.

TABLE 4

| (Na+ ion concentration) | | | | | |
|---|---|---|---|---|---|
| | 0 sec. | 5 sec. | 15 sec. | 30 sec. | 60 sec |
| L | 98.2 | 97.4 | 97.2 | 97.2 | 97.0 |
| H | 177.6 | 176.4 | 176.4 | 175.6 | 174.8 |

TABLE 5

| (K+ ion concentration) | | | | | |
|---|---|---|---|---|---|
| | 0 sec. | 5 sec. | 15 sec. | 30 sec. | 60 sec |
| L | 2.6 | 2.6 | 2.6 | 2.6 | 2.6 |
| H | 6.4 | 6.3 | 6.4 | 6.4 | 6.4 |

TABLE 6

| (Cl− ion concentration) | | | | | |
|---|---|---|---|---|---|
| | 0 sec. | 5 sec. | 15 sec. | 30 sec. | 60 sec |
| L | 65.0 | 65.2 | 64.0 | 63.6 | 62.6 |
| H | 133.6 | 132.0 | 130.8 | 129.2 | 127.0 |

Also in this case, as can be seen from tables 4 to 6, the deviation of the results obtained when the sample liquid were spotted 5 seconds, 15 seconds, 30 seconds and 60 seconds after spotting of the reference liquid from that obtained when the sample liquid was spotted simultaneously with the reference liquid are negligible though the deviation for 60 seconds is somewhat large.

The results of the first and second experiments shows that the activities of particular predetermined ions in a sample liquid can be determined with a high accuracy in accordance with the method of the present invention.

In the first experiment where the reference liquid was spotted first, the reference liquid spread over the entire area of the porous bridge before 15 seconds lapsed after spotting of the reference liquid. (The movement of the reference liquid stopped when the reference liquid spread over the entire area of the porous bridge.) When the sample liquid was spotted, the sample liquid mixed with the reference liquid contained in the portion of the porous bridge above the spotting hole to which the sample liquid was spotted. This phenomenon was observed also in the second experiment where the sample liquid was spotted first.

Conventionally it has been believed that accuracy of determination of the concentration of particular predetermined ions in a sample liquid by use of a device for measuring ionic activity is greatly affected when mixing of the sample liquid and the reference liquid takes place. However in the first and second experiments, the accuracy of determination was excellent though mixing of the sample liquid and the reference liquid took place. This result shows that the accuracy of determination of the concentration of ions is substantially not affected even if the reference liquid and the sample liquid mix with other so long as they mix in a very small amount (e.g., in an amount not larger than 1% by volume of the amount of the spotted liquids). Accordingly, in the case of a device for measuring ionic activity where the sample liquid and the reference liquid can mix with each other only in a very small amount relative to the amount of the spotted liquids as in the device for measuring ionic activity used in the above experiments, it is conceivable that the time interval between spotting of one of the reference liquid and the sample liquid and spotting of the other may be determined depending on the other factors without taking into account mixing of the reference liquid and the sample liquid. In view of the result of the above experiments, the time interval may be in the range of 0 to 60 seconds (not inclusive of 0 second) and is preferably in the range of 0 to 30 seconds (not inclusive of 0 second).

In the device for measuring ionic activity used in the above experiments, the porous bridge was formed of twisted yarn of polyethylene terephthalate, the spotting holes were 3.5 mm in diameter and the amounts of the reference liquid and the sample liquid were 50 μL. Assuming that the reference liquid and the sample liquid mixed in an amount equivalent to that contained in a part 4 mm long of the porous bridge, the amount was 0.08 μL.

Though the ion-selective electrodes were not electrically connected with each other until both the spotting holes were spotted with liquid in the device for measuring ionic activity used in the above experiments, experiments similar to the above experiments were made using devices for measuring ionic activity of a type in which the ion-selective electrodes came to be electrically connected with each other in a certain time after one of the spotting holes was spotted with liquid even if the other spotting hole was not spotted with liquid and the similar result was obtained when the other spotting hole was spotted with liquid before the ion-selective electrodes came to be electrically connected with each other by the liquid spotted to said one spotting hole.

The method for measuring electrolyte and the apparatus for measuring electrolyte of this embodiment need not be limited to those described above in conjunction with the embodiment but may be realized in other various manners.

For example, though, in the embodiment described above, the device for measuring ionic activity is held stationary in one predetermined position in the spotting station during spotting of both the reference liquid and the sample liquid, the support table may be arranged to move the device for measuring ionic activity to a first position opposed to a spotting position for one of the sample liquid spotting means and the reference liquid spotting means and then to a second position opposed to a spotting position of the other spotting means. In this case, said one spotting means need not be removed from its spotting position after spotting so long as the distance between the first and second positions are sufficient to prevent interference of said one spotting means with the other spotting means. Though the sample liquid spotting means generally must be moved from the spotting position in order to suck the sample liquid or to change the spotting tip, the reference liquid spotting means can be arranged to be kept stationary in the spotting position. It is needless to say that said one spotting means may be moved away from the device for measuring ionic activity not to interfere with the other spotting means, when the other spotting means spots the liquid to the device for measuring ionic activity, by moving said one spotting means away from its spotting position together with moving the device for measuring ionic activity from the first position to the second position.

When the support table is arranged to move the device for measuring ionic activity to the first position and to the second position from the first position, the distance between the reference liquid spotting means and the sample liquid spotting means can be sufficiently large though the driving mechanism for the support table becomes complicated in structure.

What is claimed is:

1. A method for measuring electrolyte for determining an activity of particular chosen ions in a sample liquid by use of a device for measuring ionic activity comprising an ion-selective electrode pair consisting of a pair of ion-selective electrodes which are selectively responsive to the same particular chosen ions, a pair of spotting holes through which a sample liquid and a reference liquid are respectively supplied to the ion-selective electrodes and a porous bridge which communicates the spotting holes with each other to permit the sample liquid and the reference liquid spotted to the spotting holes to electrically contact with each other, the method comprising the steps of spotting one of the sample liquid and the reference liquid to one of the spotting holes of the device for measuring ionic activity with a first spotting tool, thereafter moving at least one of the first spotting tool and the device for measuring ionic activity to remove the first spotting tool away from the device for measuring ionic activity, and then spotting the other of the sample liquid and the reference liquid to the other spotting hole of the device for measuring ionic activity with a second spotting tool within a chosen time after said one of the sample liquid and the reference liquid is spotted to said one of the spotting holes wherein the chosen time is set such that the lower limit thereof is the minimum time required to remove one spotting means away from its spotting position and to subsequently move the other spotting means to its spotting position, and the upper limit is determined based on the type of device used for measuring ionic activity.

2. A method for measuring electrolyte as defined in claim 1 in which said device for measuring ionic activity is held stationary in one position during spotting of both the sample liquid and the reference liquid, and the first spotting tool is removed away from the device for measuring ionic activity after it spots said one of the sample liquid and the reference liquid and before the second spotting tool is moved to said other spotting hole to spot said other of the sample liquid and the reference liquid to the other spotting hole of the device for measuring ionic activity.

3. A method for measuring electrolyte as defined in claim 2 in which said chosen time is longer than zero second and not longer than sixty seconds.

4. A method for measuring electrolyte as defined in claim 3 in which said chosen time is longer than zero second and not longer than thirty seconds.

5. A method for measuring electrolyte as defined in claim 1 in which said chosen time is longer than zero second and not longer than sixty seconds.

6. A method for measuring electrolyte as defined in claim 5 in which said chosen time is longer than zero second and not longer than thirty seconds.

7. An apparatus for measuring an electrolyte comprising a support table which supports a device for measuring ionic activity comprising an ion-selective electrode pair consisting of a pair of ion-selective electrodes, each of which is selectively responsive to the same ions, a pair of spotting holes through which a sample liquid and a reference liquid are respectively supplied to the ion-selective electrodes and a porous bridge which communicates the spotting holes with each other to permit the sample liquid and the reference liquid spotted to the spotting holes to electrically contact with each other, and positions the device for measuring ionic activity in a position where the sample liquid and the reference liquid are to be spotted to the respective spotting holes, a sample liquid spotting means including a sample liquid spotting tool which holds the sample liquid and spots the same to one of the spotting holes of the device for measuring ionic activity and a transfer mechanism which moves the sample liquid spotting tool between a spotting position where it spots the sample liquid to said one of the spotting holes of the device for measuring ionic activity positioned in said position and a retracted position away from the spotting position, and a reference liquid spotting means including a reference liquid spotting tool which holds the reference liquid and spots the same to the other spotting hole and a transfer mechanism which moves the reference liquid spotting tool between a spotting position where it spots the reference liquid to the other spotting hole of the device for measuring ionic activity positioned in said position and a retracted position away from the spotting position, the two spotting means being arranged so that one of the first and second spotting means first spots the corresponding liquid to the corresponding spotting hole in its spotting position and is removed away from the spotting position and then the other spotting means is moved to its spotting position to spot the corresponding liquid to the corresponding spotting hole within a chosen time after said one spotting means spots the corresponding liquid to the corresponding the spotting hole wherein the chosen time is set such that the lower limit thereof is the minimum time required to remove one spotting means away from its spotting position and to subsequently move the other spotting means to its spotting position, and the upper limit is determined based on the type of device used for measuring ionic activity.

8. An apparatus for measuring electrolyte as defined in claim 7 in which said chosen time is longer than zero second and not longer than sixty seconds.

9. An apparatus for measuring electrolyte as defined in claim 8 in which said chosen time is longer than zero second and not longer than thirty seconds.

* * * * *